(12) United States Patent
Zaruba et al.

(10) Patent No.: US 7,592,909 B2
(45) Date of Patent: Sep. 22, 2009

(54) LOCATION AND TRACKING SYSTEM USING WIRELESS TECHNOLOGY

(75) Inventors: Gergely V. Zaruba, Fort Worth, TX (US); Manfred Huber, Arlington, TX (US); Farhad A. Kamangar, Arlington, TX (US); David Levine, Fort Worth, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 110 days.

(21) Appl. No.: 11/335,337

(22) Filed: Jan. 19, 2006

(65) Prior Publication Data

US 2007/0168127 A1 Jul. 19, 2007

(51) Int. Cl.
*G08B 1/08* (2006.01)
(52) U.S. Cl. .............. 340/539.13; 340/539.21; 340/539.23; 340/825.36
(58) Field of Classification Search ............ 340/539.13, 340/573.4, 825.49, 825.36
See application file for complete search history.

(56) References Cited

U.S. PATENT DOCUMENTS 6,154,139 A * 11/2000 Heller .............. 340/573.4
6,181,253 B1 * 1/2001 Eschenbach et al. ... 340/825.37
6,753,781 B2 * 6/2004 Radomsky et al. ....... 340/573.4
7,038,584 B2 * 5/2006 Carter .............. 340/539.13
7,242,306 B2 * 7/2007 Wildman et al. ......... 340/573.1
7,283,046 B2 * 10/2007 Culpepper et al. ..... 340/539.13
2007/0132577 A1 * 6/2007 Kolavennu ............. 340/539.13

OTHER PUBLICATIONS

"Particle Filter," Wikipedia article, pp. 1-7, downloaded on Jun. 6, 2009 from http://en.wikipedia.org/wiki/Particle_filter.

* cited by examiner

*Primary Examiner*—Toan N Pham
(74) *Attorney, Agent, or Firm*—Chowdhury & Georgakis, PC

(57) ABSTRACT

A system for locating one or more objects. The system includes one or more objects having an unknown location. Each object comprises at least one mobility sensor for providing sensory information about the object, a wireless communications package for providing received signal strength indication (RSSI) and a processing unit for transmitting data about the object. The data includes the sensory information and the received signal strength indication. The system also includes at least one receiver for receiving the data about each object and at least one algorithm for processing the data about each object and identifying a location estimate about each object, thereby locating one or more objects having an unknown location.

25 Claims, 5 Drawing Sheets

LOCATION AND TRACKING SYSTEM USING WIRELESS TECHNOLOGY

CROSS-REFERENCE TO RELATED APPLICATION

Not applicable.

STATEMENT REGARDING FEDERALLY SPONSORED APPLICATIONS

Not applicable.

BACKGROUND OF THE INVENTION

The present invention relates to systems and methods for locating, orienting, and tracking one or more objects, particularly objects equipped with one or more devices or location tags using wireless network technology.

Location of objects, including items, animals and persons, is extremely important, especially when such objects are distributed over wide areas and expanses. Establishments, such as medical and health organizations, public transportation systems, banks, delivery services, the armed forces, and security systems, would benefit if they were able to locate items and personnel in their organization at any time, regardless of where they were positioned. To date, no such location or tracking system is available and there remains a need to accurately and cost-effectively identify the location of objects and/or personnel that exist as part of a larger system or organizational structure.

Existing techniques for location of objects include the use of infrared and laser systems, or sonar, radar, or satellites (global positioning systems or GPS), as examples. Unfortunately, most techniques require additional infrastructure, reference points, and/or sensors specifically for the purpose of localization. In addition, line-of-sight communication (wherein a transmitter and receiver are in visual contact with each other) is usually required with such technologies. As such, current techniques are limited in their application and use. There remains a need to offer improved location and tracking systems with minimal infrastructure components that are readily adaptable in today's high technology environment, and, in particular, to overcome the extensive infrastructure deployment issue associate with current systems.

SUMMARY OF THE INVENTION

The present invention solves many problems associated with current technologies used for localization and location of an object.

Generally, and in one form of the present invention is a system for locating one or more objects, mobile or static, using a wireless network and one or more mobility sensors. Objects, as identified herein, provide positional data about themselves, which is also used to locate, track or orient them.

The present invention takes advantage of readily available technology components, such as wireless communications systems (e.g., wireless local and/or personal area network technologies), mobility sensors (e.g., accelerometers, gyroscopes), and processing units (e.g., low-power microcontrollers) to locate and track (orient) one or more objects. Each object is provided with a wireless unit, a microcontroller and at least one mobility sensor.

In one form of the present invention, location of an object relies on received signal strength indication (RSSI) measurements from wireless access points.

In another form of the present invention, location of a first object relies on RSSI measurements obtained from other objects to determine the location of the first object. The present invention is not restricted in the number of wireless access points to provide accurate estimates of a location. Instead, the present invention uses inexpensive tools for networking purposes in combination with RSSI readings from available access point and/or from other objects in addition to filter algorithms that draw on coarse received signal strength-based localizations to provide precise location estimates.

In yet another form, the present invention provides for a method of locating and tracking (orienting) at least one object by relying on a probability distribution calculated for each object, wherein the evolving state of each object is estimated using a Bayesian filter. A recursive Bayesian filter is applied to predict all possible locations each object may have moved to from its previous location. The filtering technique used is sequential Monto Carlo filtering (also known as particle filtering or bootstrap filtering).

With the present invention, the following advantages and improvements to current location and tracking systems are featured: (a) readily available and low cost technologies are used to create one or more mesh-networked access points; (b) one-dimensional (1D), two-dimensional (2D) and/or three-dimensional (3D) mobility sensors are calibrated precisely for three-dimensional (3D) usage (i.e., with three to six degrees of freedom); (d) one or more mobility sensors are used to compensate for gravity; (e) filtered motion-based information serves as the present invention's mobility model in the filter, while RSSI readings and their use provide for a measurement model.

Another advantage of the present invention includes the fact that the systems, methods and devices of the present invention may be easily and quickly incorporated into virtually any existing organization (commercial or otherwise, including residential establishments), since most are now equipped with wireless access points. The present invention may be fitted with existing technology products, including off-the-shelf technologies, with customized or factory fitted wireless network adapters. Such wireless networking also enables mobility, a key factor in building intelligent mobile devices to perform routine tasks. Accordingly, the present invention may be incorporated into such intelligent mobile device (including household devices like vacuum cleaners and remote controls) as they become enabled with wireless technologies.

Those skilled in the art will further appreciate the above-noted features and advantages of the invention together with other important aspects thereof upon reading the detailed description that follows in conjunction with the drawings.

BRIEF DESCRIPTION OF SEVERAL VIEWS OF THE DRAWINGS

For a more complete understanding of the features and advantages of the present invention, reference is now made to the detailed description of the invention along with the accompanying figures in which corresponding numerals in the different figures refer to corresponding parts and in which.

NOTATION AND NOMENCLATURE

Figure 1:
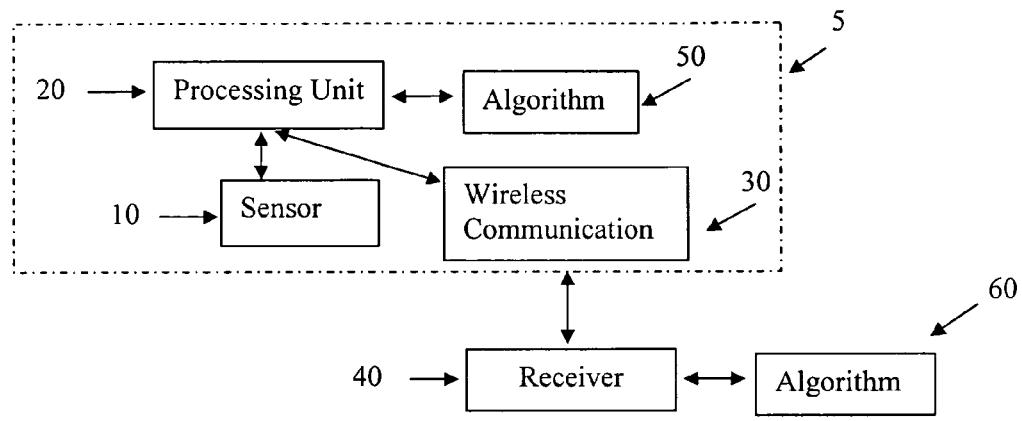
FIG. 1 depicts components of a system in accordance with one aspect of the present invention.

Certain terms are used throughout the following description and claims to refer to particular system components and configurations. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple", "couples", OR "coupled" is intended to mean either an indirect or direct electrical connection. Thus, if a first device couples to a second device, that connection may be through a direct electrical connection or though an indirect electrical connection via other devices and connections.

DETAILED DESCRIPTION OF THE INVENTION

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

The present invention is unlike previous localization techniques, in particular those using RSSI, that apply triangulation (a method of determining a relative position of an object using the geometry of triangles by applying angle measurements together with at least one known distance to calculate an object's location) or trilateration (a method of determining the relative position of an object using the geometry of triangles by applying a known location of two or more reference points and a measured distance between an object and each reference point) to compute the distance from one or more fixed points and to determine an object's location relative to such points. The present invention overcomes such narrow interpretations of location by applying a probabilistic time-series approach to RSSI. In particular, the RSSI measurement-based systems of the present invention do not require three or more reference points or additional sensor/actuator infrastructure (e.g., pressure-sensitive floors). Instead, the present invention may use readily available wireless access points or wireless access points that may be deployed for location purposed while used for other communications as well. The strength of the present invention is that RSSI readings are provided by most wireless devices as part of normal operation.

RSSI as referred to herein is a measurement of strength (not necessarily the quality) of a received signal in a wireless environment, in arbitrary units. RSSI values or measurements can represent the received signal strengths of a mobile unit or a non-mobile (e.g., fixed) unit.

Localization as referred to herein indicates, in part, that one or more objects of the present invention are aware of the location or position of one or more second objects having a location tag. Depending on implementation, the first object may be equivalent to the second object, such that one or more objects may be able to determine as well as be aware of its own location. This is important for future of ubiquitous computing environments.

According to the present invention, systems and methods for localization of at least one object are provided. Referring now to FIG. 1, an object 5 of the present invention comprises at least one mobility sensor 10 that provides sensory information (i.e., mobility information) about the object, a processing unit 20 that samples sensory information from the at least one mobility sensor and applies new calibration information to the at least one mobility sensor, and a wireless communications package 30 that receives and sends data about the object and provides RSSI readings to receiver 40. Receiver 40 is one or more fixed and/or mobile objects, each with its own processing unit that has algorithm(s) for processing the data about the object. Receiver 40 may be in the form of a second object and/or an infrastructure-based receiver (e.g., second processing unit, central processor). The data sent by wireless communications package 30 to receiver 40 includes either or both of sensory information (mobility information) and RSSI readings as further described below.

Mobility sensor 10 is any device capable of detecting physical movement (e.g., a change in motion) of the object and converting the movement into an electrical signal. Examples include an accelerometer, gravimeter, angular rate sensor, and gyroscope. Wireless communications package 30 is one that transmits information signals as electrical or electromagnetic signals via electromagnetic (e.g., radio) waves. Examples include a wireless personal area network, wireless local area network, and wireless transceiver, such as a radio-frequency [RF] digital data communication system. Examples of processing unit 20 include a microcontroller, microprocessor (e.g., highly integrated microprocessor), a single-chip microcomputer, an embedded computer and the like.

Processing unit 20 is further provided with at least one algorithm 50 to run data about object 5. Data includes filtered sensory information, mobility estimates, such as velocity and displacement, and location estimates. Algorithm 50 may include any or all algorithms that filter sensory data about the object, provide mobility estimates, and/or provide location estimates about the object. Examples of such algorithms are further described elsewhere. Accordingly, processing unit is provided with one or more features that includes (a) obtaining sensory information about the object; (b) obtaining RSSI readings about the object; (c) relaying sensory and/or RSSI data about the object to wireless communications package 30; (d) filtering sensory and/or RSSI data about the object and (e) processing sensory and/or RSSI data about the object.

As an example, an object includes two mobility sensors, a microcontroller, and a wireless transceiver. The microcontroller is associated with select algorithm(s). One mobility sensor is an accelerometer and the other is a gyroscope. The mobility sensors convert physical movement of the object into electrical signals (as mobility information). The object relays the mobility information and RSSI readings to a receiver using its wireless transceiver. The receiver received the mobility information and the RSSI readings and uses algorithm(s) to estimate the location of the object. In this example, the microcontroller does not estimate the location of the object.

In another example, an object includes two mobility sensors, a microcontroller, and a wireless transceiver. The microcontroller is associated with complete algorithm(s). One mobility sensor is an accelerometer and the other is a gyroscope. The mobility sensors convert physical movement of the object into electrical signals (as mobility information). The object estimate its own location using the algorithm(s) associated with the microcontroller based on the mobility information and its RSSI. In this example, the microcontroller provides location coordinates to a receiver.

Figure 2:
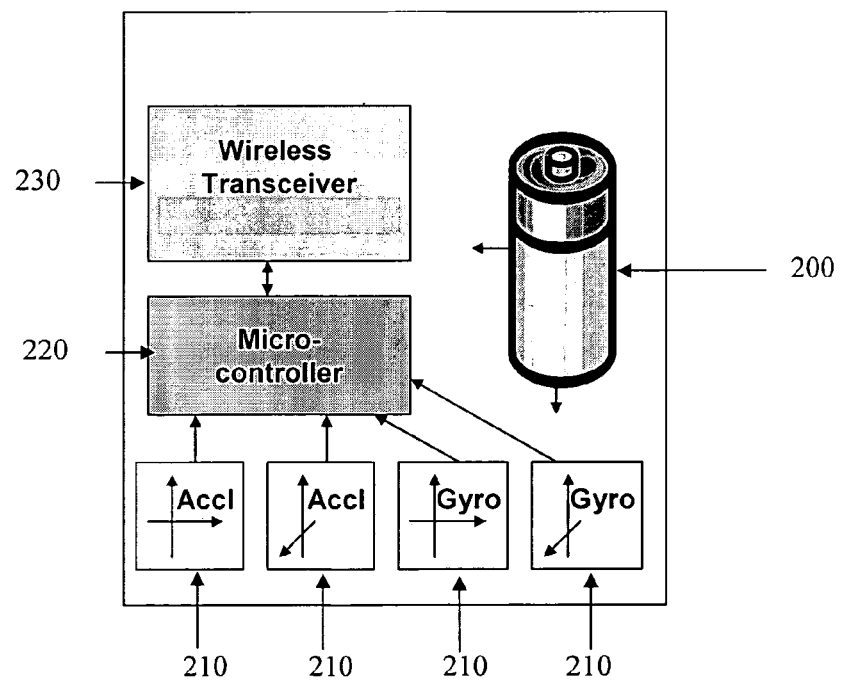
FIG. 2 depicts components of an object in accordance with one aspect of the present invention.

Objects of the present invention may be mobile or fixed. For convenience, an object as provided herein may be equipped with a tag for marking, orienting, tracking and location purposes (also referred to herein as a location tag). The location tag comprises one or more elements previously described as being associated with an object of the present invention. As shown in FIG. 2, one embodiment of location tag 200 is shown in which location tag 200 includes at least one mobility sensor 210 (e.g., accelerometer, angular rate sensor, gravimeter, gyroscope), a microcontroller 220 (e.g., highly integrated microprocessor, a single-chip microcomputer, an embedded computer) and a wireless communications package 230 (e.g., wireless local or personal area network or wireless transceiver, such as a radio-frequency [RF] digital data communication system). Microcontroller 220 may be used to help integrate mobility sensor 210 with wireless communications package 230, to collect sensory information (mobility information) as data (typically collected as sample information) about the object and/or process the sensory data (sample information).

Figure 3:
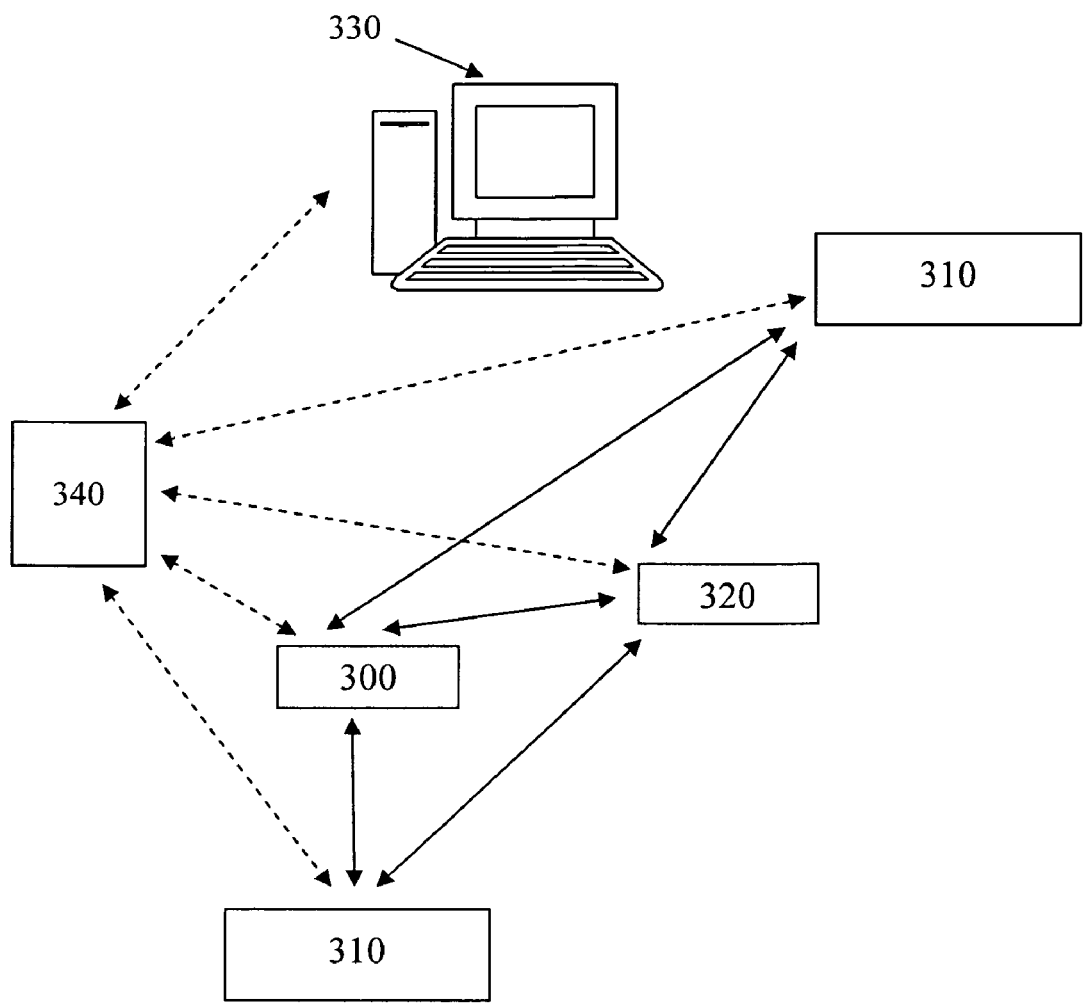
FIG. 3 depicts a system in accordance with another aspect of the present invention.

Sensory data and RSSI measurements about an object 300 are communicated (via a wireless communications system) to one or more receivers 310, 320 and/or 330 as shown in FIG. 3. The receiver(s) may be another mobile or fixed object as depicted by receiver 320, a mobile or fixed wireless access point (e.g., stationary reference point) as depicted by receivers 310), or a fixed infrastructure as depicted by receiver 330. Receiver 310 comprises similar features to that associated with object 300. Both object 300 and receiver 310 have a microcontroller and a wireless communications system; however, unlike object 300, receiver 310 does note require mobility sensor(s). As objects, neither object 300 nor receiver 320 have known locations. On the other hand, receivers 310 and receiver 330 have locations that are known either to itself or to receiver 330. In fact, receiver 330 has a known location that is predetermined.

As depicted in FIG. 3, object 300 may also receive communications (via a wireless communications system, such as radio waves) from receiver 320 and/or receiver 310 and can obtain the RSSI of such communications. Accordingly, for each object (fixed or mobile) there is an RSSI reading or measurement. In addition, for each receiver 310 there is an RSSI reading or measurement. Hence, marking, orienting, tracking and locating an object is performed using: (a) RSSI readings provided by at least one stationary reference point or fixed infrastructure (receiver 310 or receiver 330)—a process referred to herein as infrastructure localization; and/or (b) RSSI readings provided by at least one other object (receiver 320 typically having a location tag)—a process referred to herein as distributed localization. The communication range of an object as provided herein is dependent on the signals provided by the object (typically via its location tag) and the antennae 340 available for such wireless communications.

A method to obtain a location of an object as provided herein uses an algorithm that combines a measurement model using Monte Carlo signal filtering of RSSI information with a system model that uses a filtered stream from at least one mobility sensor. The measurement model using sampling data provided by an object (via RSSI) captures, follows and calculates, by sampling, a probability distribution of each location of the object at a specific time point (for positional information) or over time (tracking). By applying sampling data in the measurement model, the algorithm as provided herein is particularly useful when one or more objects are not fixed but mobile.

In general, one form of Monte Carlo filtering as used herein identifies a signal (RSSI reading) projected from an object (typically from a location tag) and calculates a probability of the object's location based on the RSSI. Another form of the algorithm is used to integrate data that includes mobility information and RSSI readings and calculate the probability distribution of the object's location given such data. An example of this is depicted in FIG. 4, box 420.

With the present invention, RSSI-based location identification of an object uses an algorithm capable of working with RSSI readings about an object and presenting location and tracking data about the object. The algorithm includes a method for filtering signals (data) about the object that reduces computational burden while providing location-space information about the object. Precise but inexpensive location estimates about an object are then presented by the algorithm. Filtering is necessary to deal with the relatively noisy nature of measurements because walls, humans, and other obstacles (mobile or fixed) affect the strength of a signal. Estimation as referred to herein is a set of techniques that compute a set of possible future states (e.g., positions) based on measurements from a known set of states.

Figure 4:
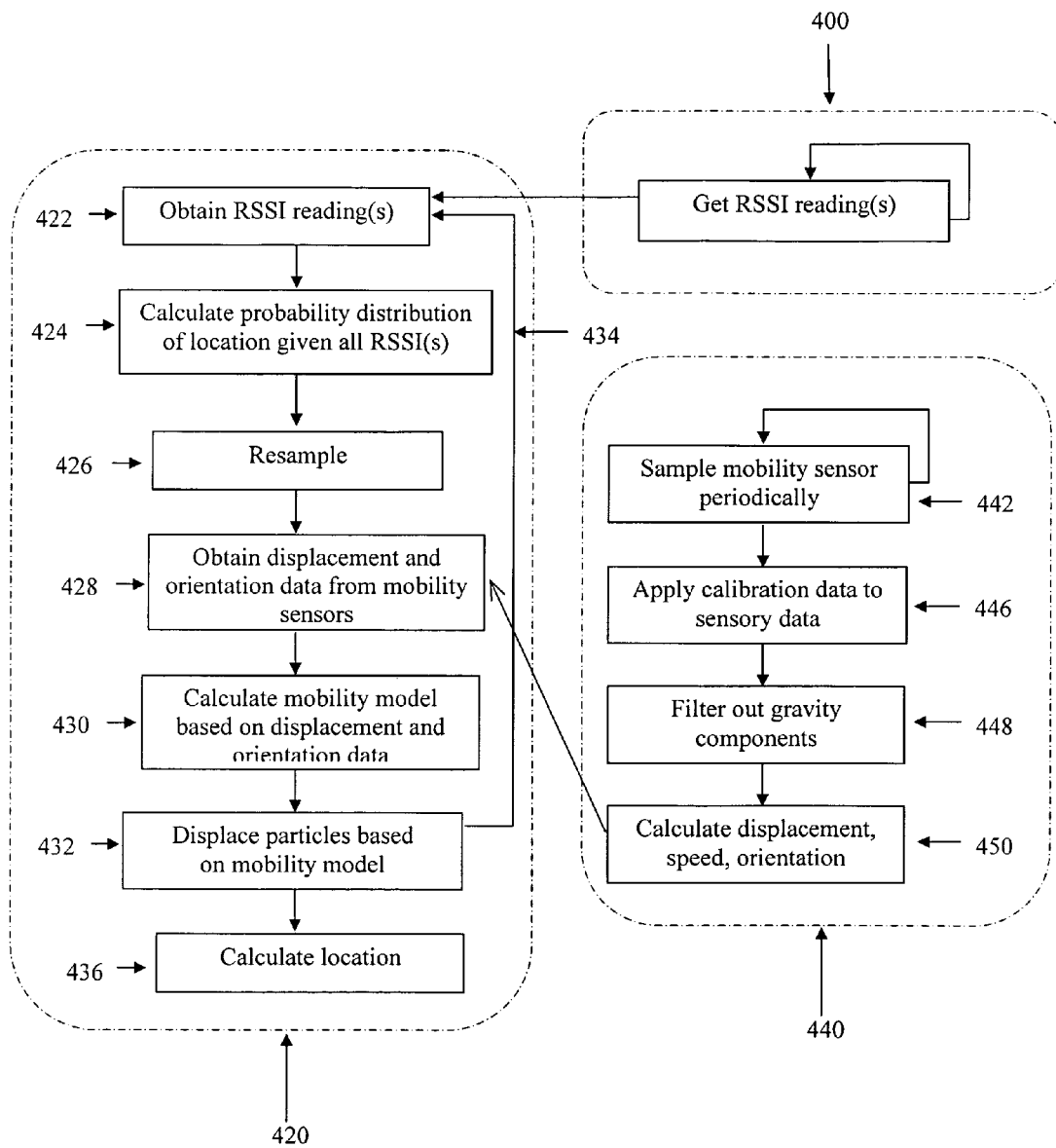
FIG. 4 depicts a representative algorithm of the present invention.

An example of algorithms of the present invention are shown in FIG. 4. Box 400 represents an algorithm in which an object samples RSSI whenever there is wireless communication from a receiver, which may occur continually or periodically. The receiver may include another mobile or fixed object typically having a location tag (as depicted by receiver 320 of FIG. 3), a mobile or fixed wireless access point (as depicted by receivers 310 of FIG. 3), or a fixed infrastructure (as depicted by receiver 330 of FIG. 3). Box 440 represents an algorithm used to provide an estimate of velocity, displacement and orientation of the object. Here an object samples each of its mobility sensors periodically for sensory data about the object (box 442) and applies calibration data to the sensory data (box 446). The calibration method is further described elsewhere. Gravity components retrieved from the one or more mobility sensors are filtered out of the sensory data (box 448) to allow for a calculation of the displacement, speed, velocity and orientation of the object (box 450).

In box 420 of FIG. 4, an iteration of an algorithm begins with box 422 in which one or more RSSI readings are obtained from one or more receivers as collected in box 400. Based on such reading(s) and with Monte-Carlo signal filtering (as a measurement model) in which the current state of particles inside the filter are used, each particle's probability is recalculated (box 424), and the probability is used to weigh the particle. A cumulative distribution of new weights of all particles is created (box 424) and used to resample each particle so they have uniform weights (box 426). This may result in one or more particles disappearing from a less likely location and being moved to a more likely location. Mobility information is then obtained in box 428 as calculated in box 450. A mobility model is created based on the mobility information obtained in box 428 (box 430) and used to move all particles (box 432). At box 432, another iteration beginning at box 422 is repeated as shown by arrow 434. In addition, an estimate for location is obtained as provided by the most likely particle or most likely value over all particles based on values associated with the displacement of particles (box 436).

With the present invention, systems and methods of object localization rely on at least one object being associated with at least one mobility sensor. The mobility sensor is used to track and locate position(s) of the at least one object. In one system, an infrastructure-based localization is provided in which one or more locations (e.g., movements) of at least one object is obtained by RSSI readings transmitted from one or more fixed access points or stationary reference points, also referred to as infrastructure). Each fixed access point knows its exact location. In such a system, a location estimate of the object is based on a fixed access point with a predetermined location; the greater the number of fixed access points, the better the location estimate obtained about each object.

Infrastructure-based localization uses RSSI readings provided by at least one access point and sensory information provided by at least one mobility sensor associated with an object. Deduction and determination of a location and/or movement of an object is obtained as an estimate via algorithms, examples of which are depicted in FIG. 4. The algorithm may be associated with the object and/or the access point. When the estimate is associated with the object, it is provided by an algorithm in operable communication with a microcontroller (also associated with the object; often through association with its location tag). In this scenario, the object is capable of providing its own location (as an estimate) that is relayed to the one or more access points of the infrastructure. As an alternative or in addition, the estimate is associated with one or more access points, so that it is provided by an algorithm in operable communication with the access point. Here, only raw signals (i.e., RSSI readings and sensory information) are relayed from the object to the access point. The raw signals are then processed either by the access point or further provided to a central source (e.g., receiver 330 of FIG. 3, a central node). An algorithm in operable communication with the access point or central source processes the raw information in order to deduct and determine the location and/or movement of the object. At any one time, one or a plurality of objects may be located by a method of parallel processing using RSSI readings (provided by at least one access point) and sensory information (provided by at least one mobility associated with each object).

Figure 5:
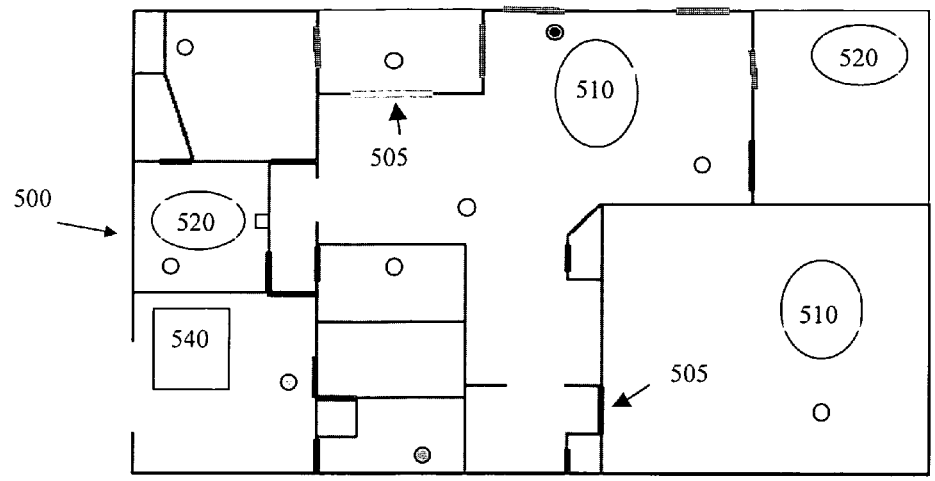
FIG. 5 depicts an example of infrastructure localization in accordance with one aspect of the present invention.

An example of infrastructure-based localization is described with reference to FIG. 5, which shows a blueprint 500 of a building and several elements of the present invention. In FIG. 5, objects 510 (e.g., person, animal, device having wheels) are each capable of moving (mobile) through the building. The building includes one or more moveable building portions, such as windows and doors as depicted by arrows 505. Each object 510 has associated with it a wireless communications package and a microcontroller/mobility sensor combination (such as IEEE 802.11b wireless transceiver with RSSI sensor that is connected to a laptop or battery powered IEEE 802.15.4). In or near the building is at least one access point 520, each associated with a wireless communications package and a microcontroller (such as IEEE 802.11b wireless transceiver or a simplified IEEE 802.15.4 without mobility sensor(s)). The location of each access point is known. The location of each object 510 may be displayed by the object itself, if it has capabilities (e.g., it is or is associated with a processing unit, such as portable laptop, hand held device, and equivalent). In addition or as an alternative, the location of each object 510, may be displayed by a local processing unit 540 (e.g. computer terminal, laptop, hand-held device or equivalent) in wireless communication with each object. Each microcontroller associated with an object (may or not be associated with a location tag) as described in this example is capable of deducing their location and movement of the object it is associated with.

A viewing of the location and movement of one or more objects (as described in FIG. 1, 3, 5 or 6) over time may be performed on a computer having a blueprint or map of an area in which the object is located. On the computer, the estimated probability density for each object is typically depicted as dots (i.e., particles) on the blueprint as shown in FIG. 7 and identified as the region that has the most dots. From this, the location estimate is calculated, as depicted by E in FIG. 7. Thus, an overall location probability is provided as broad clouds of dots and the actual estimate (E) is the area of the cloud with the highest density. FIG. 7 also provides a comparison between the estimated location E and the actual location U.

Another system of the present invention provides for distributed-based localization in which one or more locations of at least one object are obtained using RSSI readings transmitted from other mobile objects. The location of each object is not known. In such a system, a location estimate of the at least one object is based on RSSI transmissions from at least one of the other mobile objects, provided the other mobile object is associated with at least one microcontroller and a wireless communications package. Here, location estimates of the at least one object are based on location estimates provided by the other mobile objects.

Distributed localization does not require a fixed or stationary access having a known location; however, such access points may be included in certain embodiments when desired. With distributed localization, an object having at least one mobility sensor, a microcontroller and wireless communications package (may or may not be associated with a location tag) obtains location information about itself by communicating with other mobile objects, each other mobile object also associated with at least one mobility sensor, a microcontroller and wireless communications package (that may or may not be associated with a location tag). For location information, an object measures RSSI readings projected by other mobile object(s), deducts the location of other mobile object(s), and determines location information about other mobile object(s) in order to obtain its own location estimates.

Figure 6:
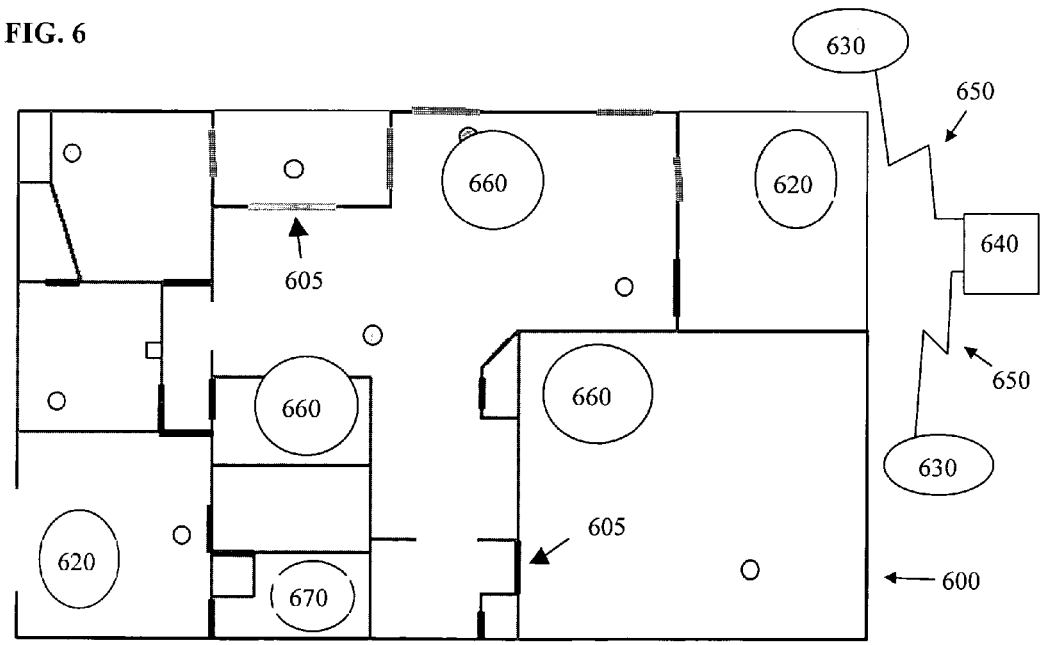
FIG. 6 depicts a representative example of distributed localization in accordance with one aspect of the present invention.
Figure 7A:
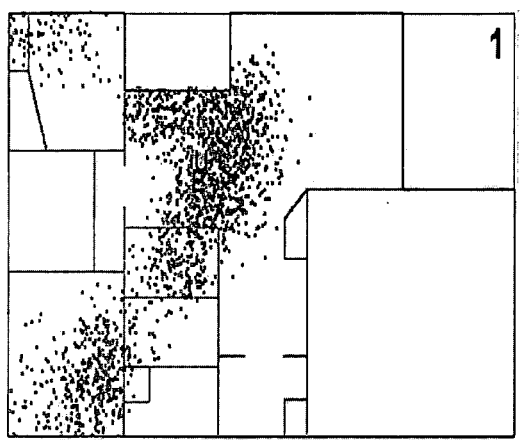
FIG. 7A shows location of an object at a first time with actual location U and estimated location E provided as region with most dots in accordance with aspects of the present disclosure.
Figure 7B:
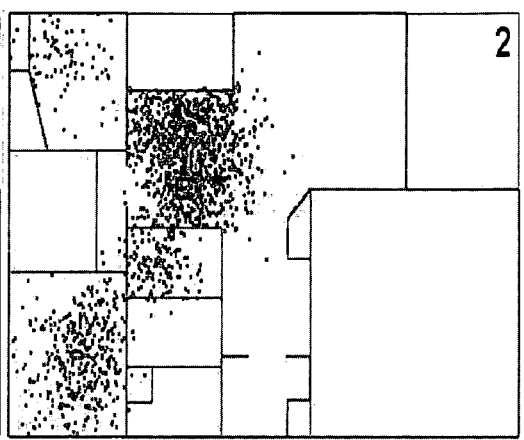
FIG. 7B shows location of an object at a second time with actual location U and estimated location E provided as region with most dots in accordance with aspects of the present disclosure.
Figure 7C:
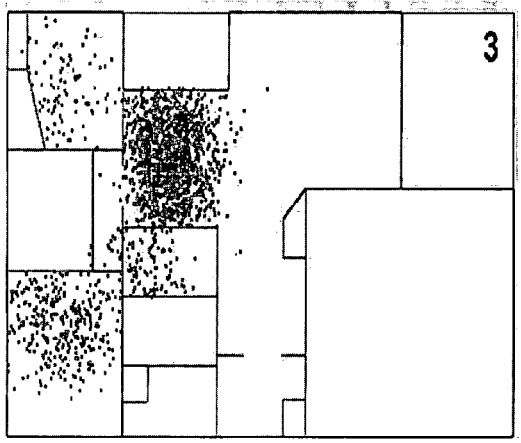
FIG. 7C shows location of an object at a third time with actual location U and estimated location E provided as region with most dots in accordance with aspects of the present disclosure.
Figure 7D:
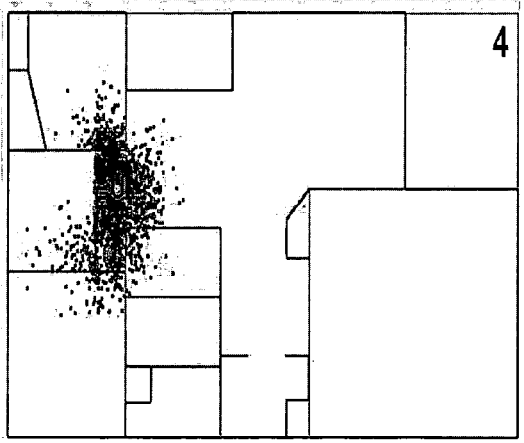
FIG. 7D shows location of an object at a fourth time with actual location U and estimated location E provided as region with most dots in accordance with aspects of the present disclosure.

An example of distributed localization is described with reference to FIG. 6, which shows a blueprint 600 of a building and several elements of the present invention. In FIG. 6, objects 610 (e.g., person, animal, device having wheels) that do not know their location but are each capable of moving (mobile) through the building are each positioned in a corner of the building. The building includes one or more moveable building portions, such as windows and doors depicted by avows 605. A transmission (and thus RSSI sensing) radius of each object 620 may be a fraction of the area of the building.

Objects 620 are each associated with a wireless communications package, a microcontroller and at least one/mobility sensor. Other mobile objects 660 are each similarly equipped and allowed to move in the building. In some instances, wireless propagation of other mobile objects 660 is limited (e.g., other mobile objects 660 only communication to each other). An estimate of a location for one of the other mobile object 660 is based on location estimates of one or more of the remaining other mobile objects 660. The location of other mobile object 660 may be displayed by each object itself, if it has capabilities (e.g., it is or is associated with a processing unit, such as portable laptop, hand held device, and equivalent). In addition or as an alternative, the location of other mobile objects 660, may be relayed and/or displayed by a base station processing unit 640 (e.g. computer terminal, laptop, hand-held device or equivalent) in wireless communication with other mobile objects 660 and capable of obtaining the location of any or all other mobile objects 660. When relaying and/or displaying information or location to a base station, at least one stationary access point 630 is in wireless communication with base station processing unit 640 (as depicted by lines 650) and with other mobile objects 660.). The location of access points 630 are known. Each access point 620 includes a microcontroller and wireless communications package and no mobility sensor(s). Because of wireless communication between other mobile object 660 and objects 620, the objects may be used to find a third object 670 having an unknown location and not associated with a wireless communications package, microcontroller or mobility sensor(s).

With the present invention, precise location estimates of one or more objects are provided with readily available and low cost technologies that increase the efficiency and cost-effectiveness of the present invention. The low cost technologies are used to create one or more mesh-networked access points capable of reading the location of one or more objects of the present invention.

Mobile sensors of the present invention are configured to obtain and produce sensory data in a three-dimensional (3-D) space; configurations include three one-dimensional mobile sensors, two two-dimensional mobile sensors and one 3-D mobile sensor. In addition, an algorithm, as depicted in FIG. 4, box 440) includes a de-warp matrix (see box 446, FIG. 4) to the raw sensory data received from the one or more mobility sensors to assist in forming the 3-D space data, in which output signals for the one or more mobile sensors may show different movement (e.g., zero acceleration) and different 1-g acceleration levels. An off-line calibration method is used to calculate the de-warp matrix using the earth's gravitational force as an accelerating force. Alternatively, the calibration may be performed using targeted forces. The calibration method is then able to provide normalized readings (e.g., using a standard mobility coordinate system). The de-warp matrix is determined for each mobile sensor configuration associated with each object and corresponds to the configuration of the sensors used therein. With the present invention, mobile sensors are biased by the gravitational force of the earth. Accordingly, to obtain acceleration values absent acceleration due this gravitational force, the earth's gravity is filtered out. Filtering is performed as depicted by box 448, FIG. 4.

In one form, the present invention is a system for locating one or more objects, mobile or static, using a wireless network and cooperating location tags. Here, each object having an unknown location may be provided with a location tag comprising at least one mobility sensor (e.g., accelerometer, angular rate sensor, gravimeter, gyroscope), a microcontroller (e.g., highly integrated microprocessor, a single-chip microcomputer, an embedded computer) and a wireless communications package (e.g., wireless local or personal area network or wireless transceiver, such as a radio-frequency [RF] digital data communication system). For convenience, the location tag may be about the size of a credit card. Other suitable sizes and/or shapes are also available as desired.

In another form of the present invention, each object as well as each receiver is provided with a device or location tag. Object location tags typically differ from receiver location tags, because receiver location tags do not require mobility sensors. In this embodiment, however, all location tags are equipped with a microcontroller and a wireless communications package. Again and for convenience, each location tag may be about the size of a credit card. Other suitable sizes and/or shapes are also available as desired.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A system, comprising:
 a movable object having an unknown location, the movable object comprising:
  at least one mobility sensor to detect physical movement of the movable object and to provide sensory information pertaining to movement of the movable object,
  a wireless communications package to provide received signal strength indication (RSSI) information, and
  a processing unit coupled to the at least one mobility sensor and to the wireless communications package, the processing unit to cause the wireless communications package to transmit data about the movable object, the data including the sensory information and the RSSI information;
 a receiver to receive the data about the movable object; and
 at least one algorithm stored in the receiver, the algorithm, when executed by the receiver, to perform operations comprising:
  creating a mobility model for the movable object, based at least in part on the sensory information from the moveable object pertaining to movement of the movable object;
  creating a measurement model for the moveable object, based at least on part on the RSSI information; and
  calculating a location estimate for the movable object, based at least in part on the mobility model and the measurement model;
 wherein the operation of creating the measurement model comprises creating a probability distribution of estimated locations for the movable object at particular points in time, based at least in part on the RSSI information;
 wherein creation of the probability distribution involves (a) calculating probabilities for particles based on current states of the particles inside the filter, (b) using the calculated probability for each particle to weigh said particle, (c) creating a cumulative distribution of new weights of all particles, and (d) using the cumulative distribution to resample each particle so the particles have uniform weights;
 wherein the operation of resampling each particle so the particles have uniform weights comprises potentially moving a particle from a less likely estimated location to a more likely estimated location; and wherein the operation of calculating the location estimate for the movable object, comprises:

displacing the resampled particles, based on the mobility model; and after displacing the resampled particles, selecting a displaced particle as the location estimate for the moveable object, based at least in part on probabilities associated with the displaced particles.

2. The system of claim 1, wherein the wireless communications package comprises a wireless transceiver.

3. The system of claim 1, wherein the at least one mobility sensor comprises at least one device from the group consisting of an accelerometer, a gravimeter, a gyroscope, and an angular rate sensor.

4. The system of claim 1, wherein the processing unit is a microprocessor, a single-chip microcomputer, or an embedded computer.

5. The system of claim 1, wherein the receiver is a second object, a stationary access point, a second processing unit, or a central processor.

6. The system of claim 1 further comprising additional objects, each comprising at least one mobility sensor, a wireless communications package and a processing unit.

7. The system of claim 1 further comprising additional receivers, each receiving the data about the movable object.

8. The system of claim 1, wherein the location of the receiver is known.

9. The system of claim 1, wherein the at least one mobility sensor, the wireless communications package and the processing unit are provided in a single device associated with the movable object.

10. A system according to claim 1, wherein the at least one algorithm uses sequential Monte Carlo signal filtering of the RSSI information to implement the measurement model.

11. A method for estimating the location of a moveable object, the method comprising:

receiving, from a movable object having an unknown location, data about the movable object, wherein the data comprises:

sensory information pertaining to movement of the movable object detected by at least one mobility sensor for the movable object, and received signal strength indication (RSSI) information from a wireless communications package for the movable object;

creating a mobility model for the movable object, based at least in part on the sensory information from the moveable object pertaining to movement of the movable object;

creating a measurement model for the moveable object, based at least on part on the RSSI information; and calculating a location estimate for the movable object, based at least in part on the mobility model and the measurement model;

wherein the operation of creating the measurement model comprises creating a probability distribution of estimated locations for the movable object at particular points in time, based at least in part on the RSSI information;

wherein creation of the probability distribution involves (a) calculating probabilities for particles based on current states of the particles inside the filter, (b) using the calculated probability for each particle to weigh said particle, (c) creating a cumulative distribution of new weights of all particles, and (d) using the cumulative distribution to resample each particle so the particles have uniform weights;

wherein the operation of resampling each particle so the particles have uniform weights comprises potentially moving a particle from a less likely estimated location to a more likely estimated location;

wherein the operation of calculating the location estimate for the movable object, comprises:

displacing the resampled particles, based on the mobility model; and after displacing the resampled particles, selecting a displaced particle as the location estimate for the moveable object, based at least in part on probabilities associated with the displaced particles.

12. The method of claim 11, wherein the mobility sensor comprises at least one device from the group consisting of an accelerometer, a gravimeter, a gyroscope, and an angular rate sensor.

13. The method of claim 11, wherein the operation of calculating the location estimate for the movable object is performed by a receiver that is a stationary access point, a processing unit, or a central processor.

14. The method of claim 11, further comprising calibrating the sensory information to provide normalized data about the movable object.

15. The method of claim 11, further comprising sampling RSSI data and combining the sampled RSSI data with cumulative sensory information about object movement to estimate displacement and location of the first movable object.

16. The method of claim 11, further comprising obtaining a de-warp matrix to apply to the sensory information.

17. The method of claim 11, further comprising automatically modifying the sensory information to compensate for gravitational forces of earth before using the sensory information and the RSSI information to calculate the location estimate for the movable object.

18. A method according to claim 11, wherein the operation of creating the measurement model comprises using sequential Monte Carlo signal filtering of the RSSI information to implement the measurement model.

19. A movable object, comprising:

at least one mobility sensor to detect physical movement of the movable object and to provide sensory information pertaining to movement of the movable object;

a wireless communications package to provide received signal strength indication (RSSI) information;

a processing unit coupled to the at least one mobility sensor and to the wireless communications package; and at least one algorithm to execute on the processing unit, the at least one algorithm to perform operations comprising:

creating a mobility model for the movable object, based at least in part on the sensory information from the moveable object pertaining to movement of the movable object;

creating a measurement model for the moveable object, based at least on part on the RSSI information; and calculating a location estimate for the movable object, based at least in part on the mobility model and the measurement model;

wherein the operation of creating the measurement model comprises creating a probability distribution of estimated locations for the movable object at particular points in time, based at least in part on the RSSI information;

wherein creation of the probability distribution involves (a) calculating probabilities for particles based on current states of the particles inside the filter, (b) using the calculated probability for each particle to weigh said particle, (c) creating a cumulative distribution of new weights of all particles, and (d) using the cumulative distribution to resample each particle so the particles have uniform weights;

wherein the operation of resampling each particle so the particles have uniform weights comprises potentially moving a particle from a less likely estimated location to a more likely estimated location; and wherein the operation of calculating the location estimate for the movable object, comprises:

displacing the resampled particles, based on the mobility model; and after displacing the resampled particles, selecting a displaced particle as the location estimate for the moveable object, based at least in part on probabilities associated with the displaced particles.

20. The movable object of claim 19, wherein the at least one mobility sensor comprises at least one device from the group consisting of an accelerometer, a gravimeter, a gyroscope, and an angular rate sensor.

21. The movable object of claim 19, wherein the movable object is the approximate size of a credit card.

22. The movable object of claim 19 further comprising control logic in the moveable object, executable by the processing unit to implement at least one algorithm.

23. The movable object of claim 19, wherein the wireless communications package comprises a wireless transceiver.

24. The movable object of claim 19, wherein the processing unit comprises a microprocessor, a single-chip microcomputer, or an embedded computer.

25. A moveable object according to claim 19, wherein the at least one algorithm uses sequential Monte Carlo signal filtering of the RSSI information to implement the measurement model.

* * * * *